United States Patent [19]

Colombo et al.

[11] 4,137,754

[45] Feb. 6, 1979

[54] MELT RHEOMETER FOR THE MEASUREMENT OF FLOW PROPERTIES OF FOAMABLE PLASTICS AND POLYMER COMPOSITIONS

[75] Inventors: Edward A. Colombo, Fairport; David E. Johnson, Macedon; James T. Tsai, Canandaigua, all of N.Y.

[73] Assignee: Mobil Oil Corporation, New York, N.Y.

[21] Appl. No.: 858,574

[22] Filed: Dec. 8, 1977

Related U.S. Application Data

[63] Continuation of Ser. No. 598,895, Jul. 24, 1975, abandoned.

[51] Int. Cl.² .......................................... G01N 11/08
[52] U.S. Cl. ...................................... 73/56; 264/40.1
[58] Field of Search ............................ 73/56, 55, 54; 264/40.1, 51, 53, 211

[56] References Cited

U.S. PATENT DOCUMENTS

| | | | |
|---|---|---|---|
| 2,987,774 | 6/1961 | Jacobson | 264/53 |
| 3,148,231 | 9/1964 | Spencer | 264/40 |
| 3,270,553 | 9/1966 | Ballman et al. | 73/56 |
| 3,287,477 | 11/1966 | Vesilind | 264/53 |
| 3,360,986 | 1/1968 | Rothschild | 73/56 |
| 3,451,103 | 6/1969 | Aykanian et al. | 264/53 |
| 3,461,498 | 8/1969 | Ramaika | 264/53 X |
| 3,627,867 | 12/1971 | Schwarz | 264/211 |
| 3,658,973 | 4/1972 | Aykanian | 264/53 |
| 3,776,989 | 12/1973 | Annis, Jr. et al. | 264/53 |
| 3,981,649 | 9/1976 | Shimano et al. | 264/40.1 X |

FOREIGN PATENT DOCUMENTS

2324099 12/1974 Fed. Rep. of Germany ............... 73/56

Primary Examiner—Richard C. Queisser
Assistant Examiner—Joseph W. Roskos
Attorney, Agent, or Firm—Charles A. Huggett; James D. Tierney

[57] ABSTRACT

An apparatus and method for the determination of the flow properties of thermoplastic materials in admixture with volatile liquids or other additives comprising an extruder which is employed to melt the polymer and admix therewith volatile blowing agents or additives. Subsequently the molten mixture is injected into an extrusion plastometer or rheometer for extruding the mixture, while still in molten form, through a capillary orifice in the extrusion plastometer. When volatile liquid blowing agents are admixed with the molten polymer in the extruder, an adjustable linkage is provided interconnecting the plastometer and the extruder whereby the pumping rate of the blowing agent can be variably adjusted and the blowing agent positively injected into the molten polymer within the extruder by the reciprocal motion of a piston means employed in the extrusion plastometer.

2 Claims, 1 Drawing Figure

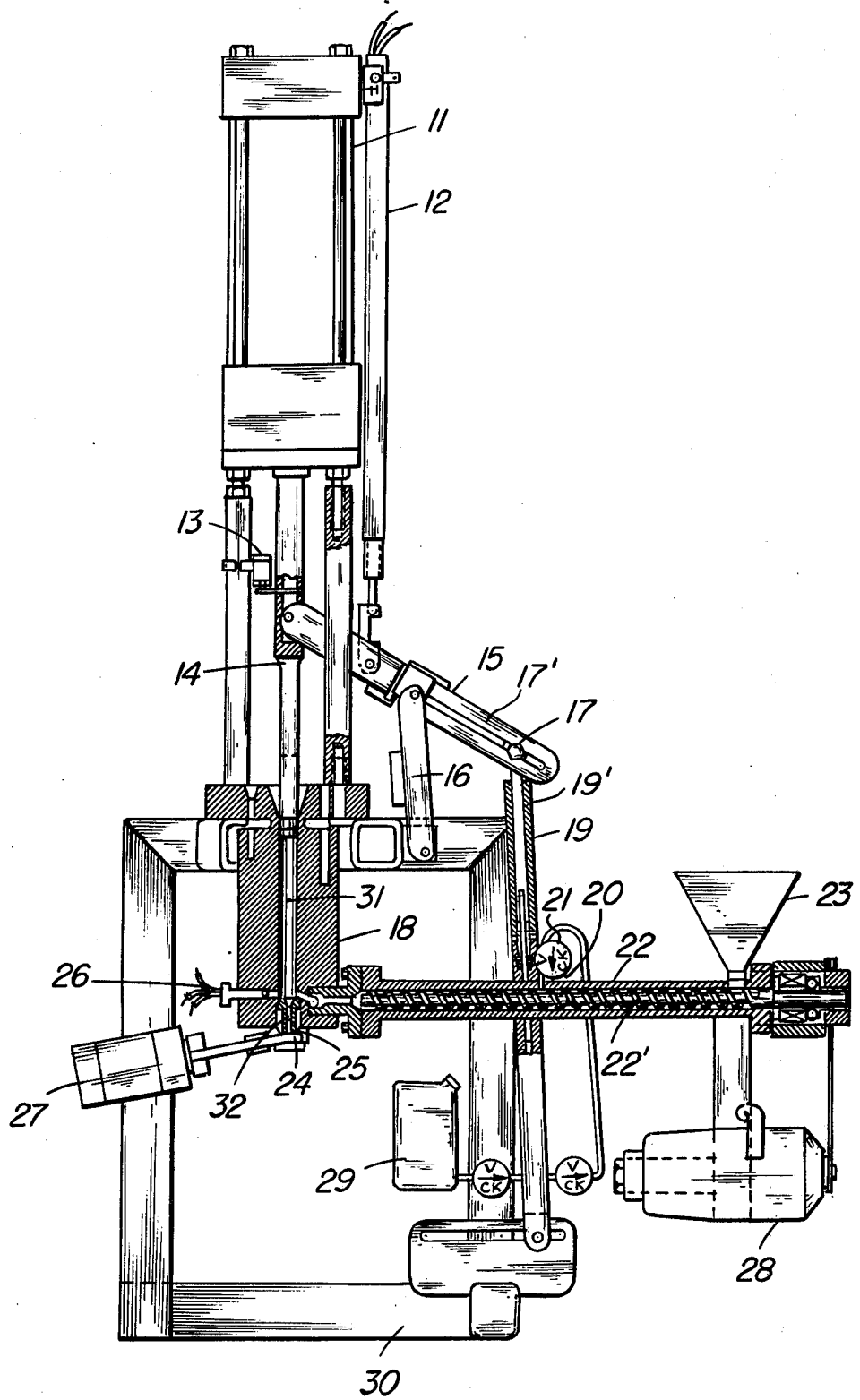

MELT RHEOMETER FOR THE MEASUREMENT OF FLOW PROPERTIES OF FOAMABLE PLASTICS AND POLYMER COMPOSITIONS

This is a continuation of Application Ser. No. 598,895, filed July 24, 1975, now abandoned.

BACKGROUND OF THE INVENTION

1. Field of the Invention

The present invention relates to an apparatus and method for measuring the rheological properties, e.g., shear stress, shear strength, die swell ratio and the like, as well as rheological changes which occur during thermoplastic foam formation and extrusion of such foam through an extrusion orifice.

2. Description of the Prior Art

In the past, activity has been reported in the literature concerned with the measurement of the rheological properties of foamed plastics (C. G. Benning, Plastics Foams, Vol. I, Wiley-InterScience, New York 1969) and molten polymers containing filler materials such as extenders (C. D. Han, Journal of Applied Polymer Science, 18, 821–829 — 1974). In such work, the rheological characterization of polymeric materials or composites is an important step in studying the various problems encountered during the processing and manufacturing of such materials during commercial operations. Due to diffusion phenomena in a highly viscous polymer melt, it is difficult to obtain flow data on a two-component mixture, one of which is a volatile liquid, e.g. molten polymers in admixture with volatile blowing agents such as isopentane, by using existing commercially available melt rheometers. Generally, in the foamed plastics areas, most of the prior art dealing with the rheological changes which occur during thermoplastic foam formation have been restricted to trial and error experimental approaches because of the lack of proper instrumentation.

Up to the present time, the most common prior art methods to evaluate molten thermoplastics containing a blowing agent have included:

(a) heating a mixture of a solid blowing agent and an inert liquid, and measuring the gaseous products which are liberated;

(b) the utilization of differential thermal analysis which measures the heat of the reactive exotherm when solid blowing agents are employed;

(c) thermal gravimetric analysis for measuring weight loss as a function of temperature (utilizing solid or liquid blowing agents); and (d) the employment of mixers such as a miniature Banbury, to measure the viscous properties of a polymeric melt as calculated from torque measurements.

The preceding methods (a), (b) and (c) are deficient in that the blowing agent decomposition behavior is determined under conditions which bear no relation to actual extrusion processes. With respect to method (d), the measurement of elastic turbulance of this type can not be directly related with processability.

Accordingly, for accurate determination of rheological properties, a standard rheometer device such as the device described in ASTM Test Designation — D 1238 — 57T, is still to be preferred for the development of research data and to assist in die design. However, such standard or typical capillary rheometer as employed in the prior art have no provision for making flow measurements on melts containing volatile liquids, i.e. blowing agents. Such devices are intended to employ starting materials which are in the form of powder, granules, strips of film or molded slugs. Such materials may be easily heated to a molten condition utilizing a heater jacket surrounding the standard rheometer device and flow measurement may be subsequently determined by extrusion of molten materials through a capillary orifice. However, it will be appreciated that a molten thermoplastic with a volatile blowing agent or an additive admixed therein constitutes a feed material which could not be readily employed with such standard devices.

The elasticity and flow characteristics of polymer melt is a major concern for the processing of plastics. These elastic effects manifest themselves in a number of ways during polymer processing such as melt fracture, sharkskin, frozen-in orientation and the like are a few examples. It has been found that these elastic effects are related to the die swell observed in the melt flow measurements. Therefor die swell measurement together with the shear stress and the shear rate measurements will provide a considerable amount of background information concerning the processability of the blowing agent in admixture with a polymer melt filled polymer and polymer composites.

SUMMARY OF THE INVENTION

The present invention relates to an apparatus and method for measuring the flow characteristics of molten thermoplastics containing, in admixture therewith, additives including volatile liquids which comprises extruder means for melting and plasticating said thermoplastic; injection means in association with said extruder means for the introduction of said additive into the thermoplastic while it is in molten form; outlet means on said extruder for the introduction of said thermoplastic additive mixture into an enclosed, heated channel; and a vertically reciprocating plunger means for forceably expressing said molten thermoplastic through a capillary orifice position as at the bottom of said channel means.

In the practice of the present invention, polymer pellets such as polystyrene may be admixed with additives such as for example nucleating agents (citric acid and sodium bicarbonate) and charged to the hopper of a thermoplastic extruder. At a point downstream from the extrusion hopper, the polymer and its additives are completely melted. At this point, a blowing agent such as isopentane is introduced by a volume displacement pump; the metering of the blowing agent is regulated by the setting of a proportioning arm hereinafter described. After the blowing agent is thoroughly mixed with the polymer melt, the mixture is pumped by the extruder through a check valve into a rheometer cylinder. A piston rod positioned for vertical reciprocating motion within the cylinder is pushed upward by the incoming molten polymer flow. The upward motion of the piston rod activates the blowing agent pump feeding the blowing agent into the extruder by motion of the proportioning arm. After the mixture in the cylinder bore reaches a desirable level, the melt simply is rated for flow measurement through a capillary orifice located on the base of the cylinder.

BRIEF DESCRIPTION OF DRAWINGS

FIG. 1 is a perspective side elevational view, partially cross-sectioned, of the melt rheometer apparatus of the present invention.

DESCRIPTION OF SPECIFIC EMBODIMENTS

As shown in FIG. 1 extruder 22 is equipped with a feed hopper 23 into which resin pellets which may be admixed with additive materials and/or cell size control additives are fed through hopper 23 into the barrel interior of extruder 22. Rotating extruder screw 22' forwards the resin mixture towards the outlet end of extruder 22. As the rotation of screw 22' advances the resin mixture heater bands (not shown) which circumscribe the exterior of extruder 22, heat the resin and cause it to become molten. As the molten resin advances past port 20 a blowing agent, such as pentane or isopentane in the case of polystyrene resin, is metered into the extruder barrel and, subsequently, advances with and is simultaneously admixed into the molten resin. As shown in FIG. 1, the rotating screw advances the molten resin through the ball check valve 34 at the outlet end of the extruder. The ball check valve allows free flow of the admixture to enter channel 31 of the rheometer portion of the device illustrated in FIG. 1. It will be noted that a ram-piston is positioned in channel 31 for reciprocal vertical movement through channel 31. Ram-piston 14 is vertically reciprocated within channel 31 by action of the reciprocating ram air cylinder 11. As the molten resinous mixture exits extruder 22, through ball check valve 34 and into channel 31, ram piston 14 is at the lower end of its stroke. Molten material continues to be metered into channel 31 forcing ram piston 14 upwardly through channel 31 against resistance of ram air cylinder 11 until channel 31 is filled to a predetermined level with the molten polymer mixture. Heating elements surround channel 31 to insure that the molten mixture is maintained at the desired temperature. Before channel 31 starts filling, capillary orifice 32 at the base of channel 31 is closed by gate valve 24, valve 24 being controlled by air cylinder 27. A thermocouple and pressure transducer 26 is located adjacent the bottom of channel 31 for measuring purposes. The process pressure is transmitted directly from the sensing diaphragm to the pressure sensing element by a liquid-filled, fine bore capillary tube. The strain gauge element delivers the electrical output needed for remote recording capability. The flush diaphragm eliminates any possibility of contamination and pluging by the process material.

It will be noted that during this operation, as ram piston 14 is being raised, one end of proportioning arm 15 which is attached to ram 14 is being raised while, as a result of its mounting on pivot link 16, the opposite end of proportioning arm 15 moves downwardly, actuating the blowing agent metering pump 19 and forcing blowing agent through check valve 21 into injection port 20 for admixture with the molten resinous material which is still upstream from the rheometer apparatus.

When it is desired to measure the rheological characteristics or flow properties of the molten polymer mixture contained in channel 31, air cylinder 27 opens gate valve 24. Ram air cylinder 11 then drives ram piston 14 downwardly through channel 31 at a controlled rate to force the molten polymer mixture through capillary orifice 32 thereby allowing precise flow rate measurements which may be calculated as follows:

The flow rate in grams per 10 minutes is calculated as follows:

$$\text{Flow rate (gm/min)} = (600\ A\ L\ d)/t$$

where $L$ = length of calibrated piston travel (cm.)
$A$ = mean of areas of piston and cylinder (cm.$^2$)
$d$ = density plastic mixture at test temperature, (gm/cm.$^3$)
$t$ = time of piston travel for length L, (minutes)

During the downward motion of ram piston 14, ball check valve 34 prevent the reverse flow of molten polymer mixture back through extruder 22. It will be noted also that the downward motion of ram piston 14 causes, by virture of pivot link 16, an upward movement of blowing agent metering pump 19 which draws a new supply of blowing agent from blowing agent reservoir 29 into metering pump 19 so that the liquid blowing agent will now be available for injection into extruder 22 during the following cycle of the apparatus as hereinabove described. It will be apparent from an inspection of the accompanying atached drawing that the raising of ram piston 14, which is caused by entry of the extruded melt into capillary bore 31 raises ram piston 14 which is subsequently lowered by air cylinder 11 to discharge melt material from capillary orifice 32. This movement respectively lowers and raises the metering pump piston ram 19' via proportioning arm 15 to respectively discharge and charge metering pump 19. It will be further noted in FIG. 1 that metering pump piston 19' is connected to proportioning arm 15 with adjusting bolt 17 in 17' for infinite pentane/polystyrene ratio adjustment from 0 to maximum. Therefore, regardless of extruder speed, the metering pump 19 always maintains the set ratio because metering pump 19 always maintains the set ratio because metering pump piston 19' moves inversely, i.e., in an opposite direction to ram piston 14, so that if extruder screw 22' increases in speed, the polystyrene feed rate increases and ram piston 14 rises faster, being driven by the molten polymer. Metering pump piston 19' proportionately will reciprocate faster via proportioning arm 15 maintaining the pentane/polystyrene mix ratio constant.

Although the apparatus and process of this invention have been illustrated with preferred embodiments, it is to be understood that modifications and variations may be employed without departing from the spirit and scope of this invention, as those skilled in the art will readily understand. Such variations and modifications are therefore considered to be within the purview and scope of the appended claims.

What is claimed is:

1. An apparatus for measuring the flow characteristics of molten plastic material which comprises an extruder means to plastify, mix and forward said plastic material into a heated retaining cylinder, piston ram means located in said cylinder, said piston ram means being vertically displaceable to express said molten plastic from said cylinder through a capillary die orifice measurement means positioned at the base of said cylinder, said apparatus being further characterized in that vertical motion of said piston ram means activates a pump means for injection of a volatile liquid into said extruder means.

2. A method for measuring the flow characteristics of a molten plastic material which comprises advancing solid plastic particles from the feed zone of a rotating screw extruder; melting and mixing said plastic in said extruder; injecting said melted plastic into a heated cylindrical chamber; forcing said molten plastic from said chamber through a capillary die orifice in said chamber while monitoring the flow characteristics of said plastic passing through said capillary die, said method being further characterized by injecting a volatile liquid blowing agent into said extruder in an amount which is proportionate to the amount of molten plastic which is being forced through said chamber through cylinder die orifice.

* * * * *